United States Patent
Van Den Berg

(10) Patent No.: US 6,332,870 B1
(45) Date of Patent: Dec. 25, 2001

(54) REGIONAL FLOW CATHETER

(75) Inventor: Paulus Cornelis Maria Van Den Berg, Amsterdam (NL)

(73) Assignee: Ideamed N.V., Curacao (AN)

( * ) Notice: Subject to any disclaimer, the term of this patent is extended or adjusted under 35 U.S.C. 154(b) by 0 days.

(21) Appl. No.: 09/424,758

(22) PCT Filed: May 29, 1998

(86) PCT No.: PCT/NL98/00316

§ 371 Date: Dec. 21, 1999

§ 102(e) Date: Dec. 21, 1999

(87) PCT Pub. No.: WO98/53735

PCT Pub. Date: Dec. 3, 1998

(30) Foreign Application Priority Data

May 30, 1997 (NL) .................................................. 1006178

(51) Int. Cl.[7] .................................................. A61B 5/02
(52) U.S. Cl. .......................... 600/504; 600/505; 600/506
(58) Field of Search .................................. 600/504, 505, 600/506, 507, 484, 485, 486, 488, 468, 547, 526, 372, 373, 381

(56) References Cited

U.S. PATENT DOCUMENTS

| | | |
|---|---|---|
| 3,896,373 | 7/1975 | Zelby . |
| 3,995,623 | 12/1976 | Blake et al. . |
| 4,911,174 | 3/1990 | Pederson et al. . |
| 5,029,585 | 7/1991 | Lieber et al. . |
| 5,174,299 | * 12/1992 | Nelson .................................. 600/505 |
| 5,520,178 | * 5/1996 | Dahn et al. ........................... 600/368 |
| 5,531,714 | * 7/1996 | Dahn et al. ........................... 604/264 |
| 5,682,899 | * 11/1997 | Nashef et al. ......................... 600/505 |

FOREIGN PATENT DOCUMENTS

| | | |
|---|---|---|
| 2 180 072 | 3/1987 | (GB) . |
| 2 187 100 | 9/1987 | (GB) . |
| WO 96/35476 | 11/1996 | (WO) . |

* cited by examiner

*Primary Examiner*—John P. Lacyk
*Assistant Examiner*—Navin Natnithithadha
(74) *Attorney, Agent, or Firm*—Young & Thompson

(57) ABSTRACT

In use of at least two electrode pairs for the generation of a difference signal that corresponds to the flow through a vein upstream and downstream of the connection of a venous duct to the vein, a first signal is generated that corresponds to the resistance over the first electrode pair, upstream of the connection of the venous duct to the vein, a second signal is generated that corresponds to the resistance over the second electrode pair, downstream of the connection of the venous duct to the vein, and the difference signal between the first and the second signal is then determined so that a regional blood flow through a person or an animal can be determined.

13 Claims, 1 Drawing Sheet

REGIONAL FLOW CATHETER

BODY OF THE INVENTION

The present invention relates to the use of at least two electrode pairs in the generation if a difference signal that corresponds to the flow through a vein upstream and downstream of the connection of a venous duct to said vein.

In the present invention no protection is requested for operations which fall within the scope of Article 52, paragraph 4 of the European Patent Convention or comparable provisions under national law.

No measurement methods for determining the distribution of the blood flow in a person or an animal over the organs and the limbs are disclosed in the prior art. However, it is clear that more information on the blood distribution and in particular information on regional flow distribution would be an enormous asset in determining the condition of a person and for making a diagnosis. The serious pathophysiological abnormalities with which physicians are confronted nowadays and the widespread use of very powerful drugs which have an effect on the circulation underline the need which exists for more information on the cardiovascular system.

Only recently it became generally known that the cardiac output is to a significant extent determined by changes which occur in the distribution of the blood flow and that the output is not determined solely by the factors which determine the functioning of the heart. These factors are, inter alia, the preload, the afterload, contractility and the heart rate. Quantitative information on the regional blood flow is therefore of great importance in order to make headway in respect of diagnosis, evaluation of the functional status of the cardiovascular system and the treatment thereof in the case of seriously ill patients. The problem of the interpretation of haemodynamic measured data is further complicated by the fact that the cardiovascular system is a closed circuit, with all variables influencing one another. That is why an evaluation of the cardiovascular system without taking account of information on the blood flow distribution is a risky undertaking which can lead to misleading conclusions and thus can be harmful to the patient.

To summarise, it can be stated that the evaluation of the haemodynamic status of a seriously ill patient cannot be based solely on parameters which determine the performance of the heart because other factors, such as, for example, the blood flow distribution, are of crucial importance for the functioning of the circulation system.

SUMMARY OF THE INVENTION

The aim of the present invention is to provide a method and an apparatus for determining the regional blood flow from and to the various organs and limbs in a person or in a mammal.

In a first aspect, the present invention therefore relates to the use of at least two electrode pairs in the generation of a difference signal that corresponds to the flow through a vein upstream and downstream of the connection of a venous duct to said vein,
wherein
- a first signal is generated that corresponds to the resistance over the first electrode pair, located upstream of the connection of the venous duct to the vem;
- a second signal is generated that corresponds to the resistance over the second electrode pair, located downstream of the connection of the venous duct to the vein; and then
- the difference signal between the first and the second signal is determined.

The difference signal that is obtained in this way can, if desired, be converted with the aid of analogue or digital means into a regional blood flow. The advantage of such an application is that the contribution of the various venous ducts to the blood flow in a main vessel can be determined in any desired outflow region of a patient. In this way the regional blood flow can be determined in situ. As a result of also using electrode pairs, no point measurements are made in the blood vessel but the blood flow is determined over a segment of a vein. The result of such a segmental measurement is much more accurate than that of a point measurement which, for example, would be carried out using a thermometer.

The generation of the difference signal is further facilitated if the electrodes are placed on a catheter.

In a second aspect, the present invention relates to a catheter for the generation of a difference signal that corresponds to the flow through a vein upstream and downstream of a connection of a venous duct to said vein. The catheter according to the present invention comprises an essentially tubular catheter element, provided close to the end thereof with a number of measurement electrodes, which are connected by means of leads to a connection element for connecting the measurement electrodes to a power source and/or a monitor. The catheter according to the present invention is characterised in that the measurement electrodes are mounted on the catheter element such that the measurement electrodes of a catheter element inserted in a main vein are located downstream with respect to the respective connections of the venous ducts to the main vein.

In a particular embodiment the distance between the measurement electrodes and the end of the catheter element essentially corresponds to the distance spanned by the venae cavae, from the opening into the right atrium to the respective connections of the venous ducts to the venae cavae. The advantage of such a regional flow catheter is that it is possible to measure the regional blood flow and thus the distribution of the blood over the intestines and the liver, the kidneys, the legs and the arms and the head. A measurement of this type provides a physician with an accurate picture of the condition of the cardiovascular system of a person. Moreover, the regional blood flow measurement offers the possibility of intervention at an early stage when changes occur in the blood circulation. Long before changes in the systemic blood pressure and the cardiac output can be recorded, compensation mechanisms are active in the event of threatening decompensation of the cardiovascular system, the blood flow being fed to the most vital organs. A very early detection of a possible circulatory dysfunction is possible by measuring the regional blood flow.

In another embodiment of the catheter according to the present invention for use in the vena cava inferior the measurement electrodes are mounted on the catheter element 140–220 mm, preferably 175 mm, away from the end of the catheter element. With this embodiment it is advantageous that five first measurement electrodes with a mutual spacing of 4–8 mm, preferably 5 mm, are mounted on the catheter element, one of said first measurement electrodes being positioned 4–8 mm, preferably 5 mm, away from the end of the catheter element. The catheter according to the present invention for use in the vena cava inferior is further improved in that six second measurement electrodes with a mutual spacing of 20–30 mm, preferably 25 mm, are mounted on the catheter element, the distance between that first measurement electrode which is positioned furthest from the end and that second measurement electrode positioned closest to the end being 20–30 mm, preferably 25 mm. The advantage of these measures is that on introducing the catheter into the vena cava inferior as far as the right atrium, the measurement electrodes are downstream with respect to the connections of the venous ducts to the vena cava inferior. Consequently, the blood supply from said venous ducts can be determined using said measurement electrodes.

Yet a further embodiment of the catheter according to the present invention for use in the vena cava superior is characterised in that the measurement electrodes are positioned 200–400 mm away from the end of the catheter element, the mutual spacing being 10–20 mm. The advantage of this is that on introducing the catheter into the vena cava superior as far as the right atrium, the measurement electrodes are located downstream with respect to the connections of the venous ducts to the vena cava superior. As a result of this measure, the blood supply from said venous ducts towards the heart can consequently be determined using the measurement electrodes.

The aim with the catheter according to the present invention is that an outflow opening is made in the catheter element, the outflow opening being made further away from the end of the catheter element than at least two of the measurement electrodes fixed to the catheter element. The advantage of this is that fluid which has an electrical resistance other than that of the blood itself can be supplied through the outflow opening. By this means the change in voltage over the measurement electrodes in the downstream direction can be altered.

The catheter according to the present invention is further improved in that calibration electrodes are mounted on the catheter element, the calibration electrodes being mounted further away from the end of the catheter element than the outflow opening and the mutual spacing between said calibration electrodes being 0.1–0.5 mm. Positioning calibration electrodes on the catheter enables the electrical resistance of the blood to be accurately determined before or during the blood flow measurements. Because the calibration electrodes are further away from the end of the catheter element than is the outflow opening, the electrical resistance over the calibration electrodes does not change when fluid having an electrical resistance other than that of the blood itself is supplied via the outflow opening. An ancillary advantage of positioning the calibration electrodes further away from the catheter end than the outflow opening is that the recirculation can be measured using the calibration electrodes. When the blood (with the added fluid therein) flows, via the heart, the lungs, the arteries and organs, once again through the vein in which the catheter has been introduced, this recirculation can be determined by means of the calibration electrodes.

The catheter according to the present invention is also improved in that the measurement electrodes are annular electrodes. This means that the electrodes are formed by annular elements which, for example, are partially sunken into the catheter element.

A similar catheter with annular electrodes is disclosed in U.S. Pat. No. 4,951,682. This catheter is intended for measuring the volume of the right atrium. For such a volume measurement, the end of the catheter is positioned in the right atrium. That end of the catheter is provided with a number of electrodes. A voltage difference is applied to the two outermost measurement electrodes. The change in voltage over the path between the outermost electrodes is then measured using the intervening measurement electrodes. The size of the right atrium can be determined from the measured change in voltage.

With the catheter according to U.S. Pat. No. 4,951,682 it is not possible to measure a regional blood flow in accordance with the use and the catheter according to the present invention because the positioning of the electrodes on the catheter element is not such that the measurement electrodes on a catheter introduced as far as the heart are located on either side of the connections of venous ducts to a main vein.

Furthermore, there are the following differences between the catheter according to the present invention and the catheter according to U.S. Pat. No. 4,951,682:

The catheter according to U.S. Pat. No. 4,951,682 has an inflatable portion (60) at the end thereof The inflatable portion (60) is required in order to be able to close off the pulmonary artery (108) when carrying out a volume measurement in the heart. In the case of a measurement with the catheter according to the present invention no vein or artery whatsoever is closed off and such a balloon is therefore not required.

The catheter according to U.S. Pat. No. 4,951,682 comprises a reinforcing element (90) as a mandatory requirement for correct positioning of the catheter in the heart. The catheter according to the present invention is not placed in the heart and a reinforcing element is therefore not required.

The catheter according to U.S. Pat. No. 4,951,682 also preferably comprises a thermistor (82). Such a thermistor is not necessary when using the catheter according to the present invention.

The measurement electrodes on the catheter according to U.S. Pat. No. 4,951,682 are located 90 mm to 200 mm away from the end thereof, preferably 90 mm to 164 mm away. Placing the electrodes such a distance away from the end renders measurement of the regional blood distribution through the venae cavae impossible with the catheter according to U.S. Pat. No. 4,951,682. The measurement electrodes on the catheter according to the present invention are therefore located 140–220 mm, preferably approximately 175 mm, away from the end (for use in the vena cava inferior) or 200–400 mm away from the end (use in the vena cava superior).

The functioning of the apparatus according to the present invention will be further illustrated with reference to the following figures, in which:

DESCRIPTION OF THE PREFERRED EMBODIMENT

Figure 1:
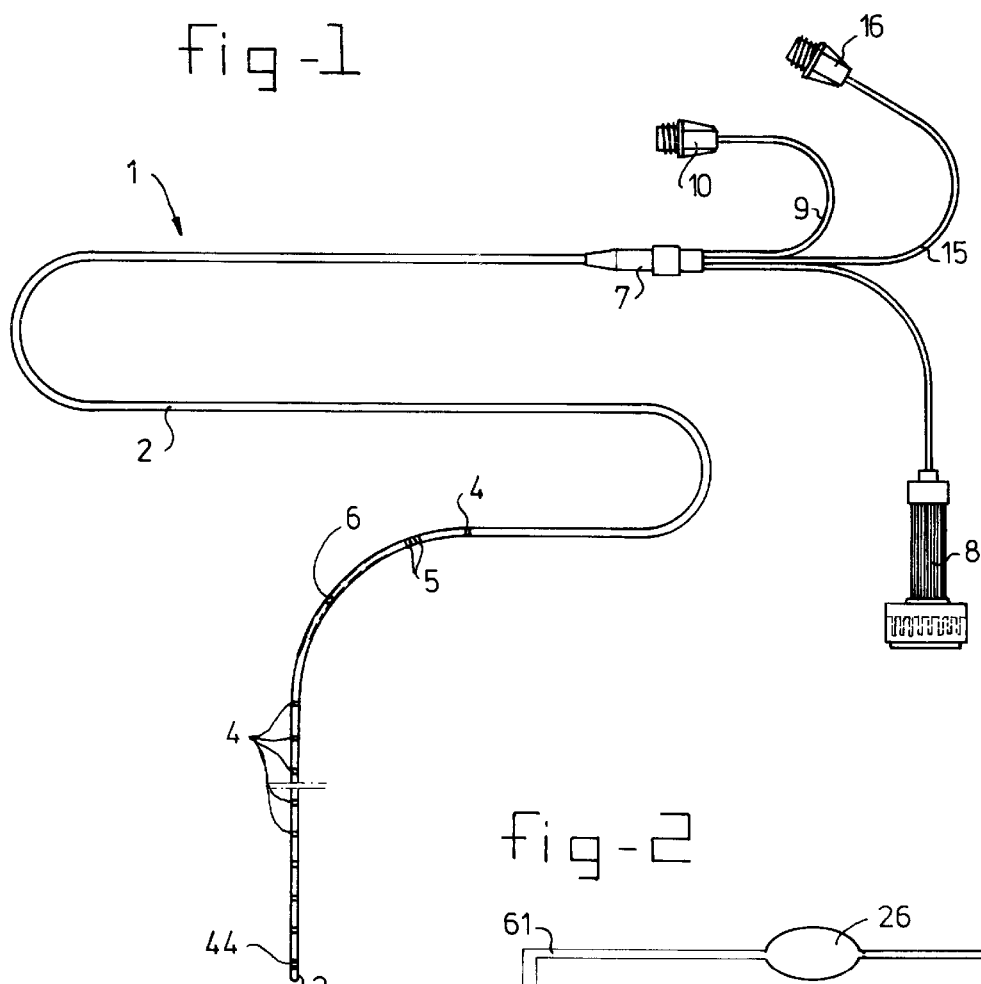
FIG. 1 is a view of the regional flow catheter according to the present invention.

FIG. 1 shows the catheter for measuring a regional blood flow through a vein according to the present invention, said catheter being indicated in its entirety by 1. The regional flow catheter 1 comprises a long, thin preferably tubular, flexible catheter element 2, the end 3 of which has been modified for introduction into a venous blood vessel. Measurement electrodes 4 are fixed to the catheter element 2 close to the end 3. An outflow opening 6 has been made further away from the end 3. Two calibration electrodes 5 may have been fixed to the catheter element 2 between said outflow opening 6 and the measurement electrodes 4. The regional flow catheter 1 further comprises a connector 7 by means of which the flexible catheter element 2 is connected to, inter alia, a plug 8. The measurement electrodes 4 and the calibration electrodes 5 are connected to the plug 8 with the aid of power leads, which, for example, are placed in the wall of the catheter element 2. The plug 8 can be connected to, for example, a monitor and/or a power source. In this way voltage can be applied to the electrodes 4 and 5 and the measured voltage difference between the electrodes can be displayed with the aid of a monitor. The connector 7 is also connected to a first fluid line 9 provided with a connection element 10. Said fluid line 9 is connected to an open end 3 of the catheter element 2, for example, by means of a channel in the wall of the catheter element 2 or via the interior of a tubular catheter element 2. Via the connection element 10, the fluid line 9 and the catheter element 2 it is then possible, for example, to supply a medicine to the blood vessel via the outflow opening 3. The connector 7 is also connected to a second fluid line 15 provided with a connecting element 16. With the aid of said fluid line 15 fluid can be fed to the outflow opening 6 upstream with respect to the measurement electrodes 4 and the calibration electrodes 5. The electrical resistance between the electrodes 4 can then be adjusted with the aid of said fluid when a catheter element 2 is introduced into a blood vessel.

To determine a regional blood flow, the catheter 1 is placed in a vein. During this operation the catheter 1 is so positioned that there is at least one pair of electrodes 4 on either side of the connection of a venous duct to said vein. In the present invention the vessels through which the blood flows towards the main veins such as, for example, the venae cavae, are termed the venous ducts. In the present invention 'downstream' with reference to the direction of flow into the veins means towards the heart; 'upstream' with reference to the direction of flow through the veins means away from the heart.

The electrical resistance of the blood over a segment of the main vein is measured using the electrodes 4. A specific quantity of physiological saline is then introduced into the main vein via the outflow opening 6. This causes the electrical resistance of the blood to change. The rate at which the measured resistance returns to the level prior to the addition of the physiological saline is a measure for the flow rate of the blood in the main vein. By now measuring the flow rate through the main vein upstream and downstream of the connection of the venous duct to the main vein, the quantity of blood which flows through the venous duct into the main vein can be measured. This means that the quantity of blood that has flowed through the region of the body which is upstream of the venous duct is measured by this means. The regional blood flow through part of the body is thus determined in this way.

Figure 2:
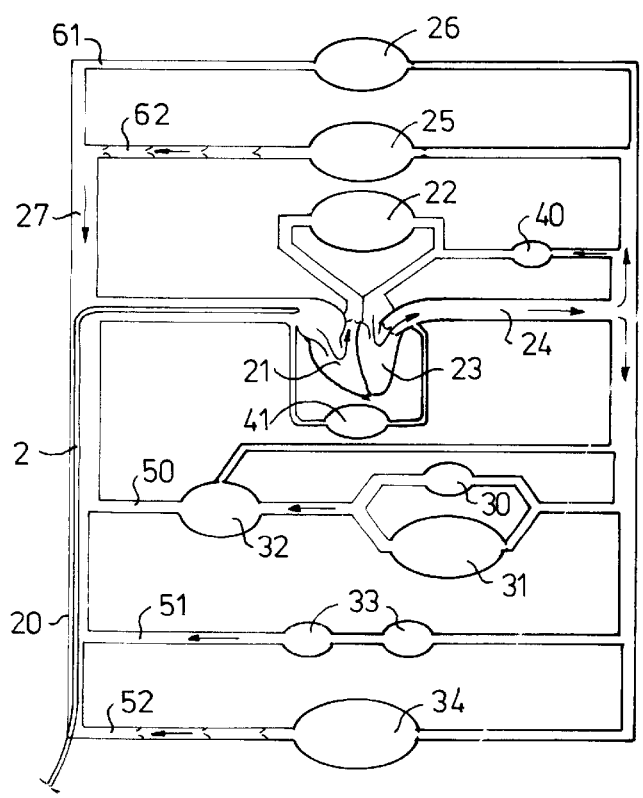
FIG. 2 is a diagrammatic overview of the blood circulation in a person, with the regional flow catheter according to the present invention introduced therein.

The functioning of the regional flow catheter 1 according to the present invention when the catheter element 2 has been introduced into the vena cava inferior 20 is shown diagrammatically in FIG. 2, which shows the blood circulation in a person.

The blood flows from the right atrium 21 via the lungs 22 to the left atrium 23 and then via the aorta 24 via the arms 25 and the head 26 through the vena cava superior 27 back towards the right atrium 21. The blood also flows via the spleen 30, the intestines 34 and the liver 32, via the kidneys 33, and via the legs 34 through the vena cava inferior back to the right atrium. The tracheal branches 40 and the coronary vessels 41 are also shown in the figure.

The blood flows essentially via three venous ducts back to the vena cava inferior 20. The blood that has flowed through the spleen 30, the intestines 31 and the liver 32 is supplied via the venous duct 50. The blood that has flowed through the kidneys 33 is supplied via the second venous duct 51. The blood that has flowed through the legs 34 is supplied via the venous duct 52. The regional blood flow, i.e. the quantity of blood that is supplied by the duct 50, 51 or 52, respectively, can be measured using the measurement electrodes 4 on the catheter element 2 in the vena cava inferior 20.

A measurement proceeds as follows: the catheter element 2 is introduced into the vena cava inferior 20 and inserted until the end 3 of the catheter is in the right atrium of the heart 21. This positioning of the end 3 in the right atrium 21 of the heart can, for example, take place accurately because a pair of reference electrodes 44 have been mounted close to the end 3 of the catheter element 2, by means of which reference electrodes a sudden change in diameter can be detected at the point in time when the end 3 of the catheter element 2 is inserted into the right atrium 21. The positioning of the measurement electrodes 4 on the catheter element 2 must be such that there is at least one pair of electrodes 4 on either side of the connections of the venous ducts (50, 51, 52, 61, 62) to the venae cavae (20, 27), the contribution of which to the total blood flow through the venae cavae (20, 27) is to be measured. For use in the vena cava inferior 20, this means that preferably the first electrode 4 is 4–8 mm, preferably approximately 5 mm, away from the end 3 of the catheter element 2. The next four measurement electrodes 4 after said first electrode 4 at the end 3 of the catheter element 2 also have a mutual spacing of 4–8 mm, preferably approximately 5 mm. The subsequent six measurement electrodes 4 have a mutual spacing of 25 mm (20–30 mm). The outflow opening 6 is located even further away from the end 3 of the catheter element 2.

Calibration electrodes can also be positioned on the catheter element 2. These electrodes have a mutual spacing of 0.1 mm (0.1–0.5 mm). Because of the small spacing between these electrodes, only the very local specific resistance of the blood is determined. The packed cell volume of the blood can be calculated from this. This electrode is then used to determine the recirculation, so that account can be taken of this during measurement of the blood flow. A current with a constant amplitude of 30 Ma (RMS) with a frequency of 25 Khz is then applied between the two outermost measurement electrodes 4. This results in an electrical field, the voltage of which can be measured between the various intervening successive measurement electrodes 4. The voltage is a measure for the resistance between the various electrodes 4, by means of which partial flow measurements can be determined. Depending on the anatomical relationships and dimensions, the regional blood flow originating from the ducts 50, 51 and 52 can be measured in accordance with the said principle in any desired region of the vena cava inferior.

It is clear that the positioning of the measurement electrodes 4 on the catheter element 2 for use of the regional flow catheter 1 in the vena cava inferior 20 differs from the positioning of the measurement electrodes 4 on a catheter element 2 for use in the vena cava superior 27. When the regional flow catheter 1 is used in the vena cava superior 27, the measurement electrodes are located 200 to 400 mm away from the end 3 of the catheter element 2, the measurement electrodes 4 having a mutual spacing of 10 to 20 mm, so that the supply by the venous ducts 61 and 62 to said vena cava superior 27 can be measured. In this case the outflow opening 6 is about 420 mm away from the end 3 of the catheter element 2.

It must be understood that the values quoted here for the spacings between the measurement electrodes 4 on the catheter element are average values. If a catheter according to the present invention were to be used for a patient of a different size (children, newborn babies or animals), these spacings can, of course, be adjusted as desired.

The use of the regional flow catheter 1 according to the present invention is based on the following measurement principle: when a fluid with a different electrical resistance is injected into a bloodstream, the resistance in the blood vessel changes in the downstream direction. The resistance which changes over time is related to the flow between two successive measurement electrodes 4. The flow between the said electrodes 4 can be determined using the modified Stewart-Hamilton equation. The following equation applies:

$$\text{Flow} = (60 \times m)/ct$$

where:

Flow=local blood flow measured in blood vessel (venous)
m=injected quantity of indicator
c=average change in the resistance
t=time over which resistance is changed The local blood flow can then be determined taking account of correction factors for the packed cell volume of blood, the sodium content, the temperature of the blood and the flow rate. One of the advantages of the use of this conductance-dilution method is firstly that complete mixing between the blood and the injected fluid is not necessary in order to obtain a good measurement. A measurement result is, after all, based on the measurement of the resistance between two electrodes 4, which are positioned with a mutual spacing of at least a few millimeters. With this arrangement the resistance is essentially determined by the volume of blood present between said electrodes 4. Thus, with the conductance-dilution method use is made of a field measurement and this has hardly any dependence on the mixing of the injected fluid in the blood. A reproducible value of the change in resistance dependent on the blood flow can be determined even in an inhomogeneous field.

A second advantage is that there is no indicator loss with the measurement method according to the present invention. The measured signals therefore also do not have to be compensated for any possible indicator loss.

By mounting the two additional calibration electrodes 5, by means of which the measurement can be calibrated, it is also possible to measure the recirculation. The final values which are determined with the regional flow catheter 1 according to the present invention can be corrected for recirculation in this way.

To summarise, it can be stated that with the aid of the regional flow catheter 1 according to the present invention it is possible to determine the flow rate in the bloodstream over a number of segments in a blood vessel, either through the venae cavae (as shown in FIGS. 1 and 2) or through any other outflow region. For this determination a blood vessel is divided into a number of segments equal to the number of measurement electrodes 4 minus 1. In this way the increase in the blood flow in a blood vessel as a consequence of the supply of blood to the main stream can be measured and the regional blood flow through a person or an animal can thus be determined.

A number of embodiments of a catheter with a limited number of measurement electrodes thereon are discussed in the present invention. In principle it would be possible to make a catheter with a large number of electrodes thereon. Depending on the location in the body where the catheter is introduced, only some of these electrodes are then used for a measurement. A 'universal' catheter can thus be produced by positioning a large number of electrodes on the catheter element.

What is claimed is:

1. Method for measuring the flow through a vein, the vein being connected to at least a venous duct, comprising the steps of:

generating a first signal that corresponds to the resistance over a first electrode pair, the first electrode pair being located upstream of the connection of the venous duct to the vein;

generating a second signal that corresponds to the resistance over a second electrode pair, the second electrode pair being located downstream of the connection of the venous duct to the vein;

determining the difference signal between the first and the second signal; and converting the difference signal into the flow through the vein with the aid of analogue or digital means.

2. Method according to claim 1, characterized in that the electrodes are positioned on a catheter.

3. Catheter for determining the flow through a vein upstream and downstream of the connection of a venous duct to said vein, comprising:

an essentially tubular catheter element;

the distal end of the tubular catheter element being provided with a number of primary measurement electrodes;

the electrodes being connected by leads to a connection element for connecting the primary measurement electrodes to a power source and/or a monitor; and an outflow opening positioned in the catheter element, the catheter element being suitable for insertion in a vein into which at least one venous duct opens, wherein, the catheter element (2) is provided with secondary measurement electrodes positioned on the catheter element (2) away from the distal end (3), and the catheter element (2) has a length for positioning at least a first pair of measurement electrodes (4) upstream with respect to the connection of said venous duct to the vein generating a first signal that corresponds to the resistance over said first electrode pair and for positioning at least a second pair of measurement electrodes (4) downstream with respect to said connection generating a second signal that corresponds to the resistance over said second electrode pair, the difference signal between said first and second signal being a measure for the contribution of said venous duct to the flow through said vein.

4. Catheter according to claim 3, wherein, said catheter is suitable for insertion in the venae cavae, the catheter element (2) has a length for introducing the distal end (3) thereof in the venae cavae (20, 27) as far as the opening into the right atrium (21), the position in which the distal end is introduced in the right atrium (21), at least one pair of measurement electrodes (4) is located upstream with respect to the respective connections of the venous ducts (50, 51, 52, 61, 62) to the venae cavae (20, 27) generating a first signal that corresponds to the resistance over said first electrode pair and at least one pair of measurement electrodes (4) is located downstream with respect to the respective connections of the venous ducts (50, 51, 52, 61, 62) to the venae cavae (20, 27) generating a second signal that corresponds to the resistance over said second electrode pair, the difference signal between said first and second signal being a measure for the contribution of said venous duct to flow through said venae cavae.

5. Catheter according to claim 3 wherein, the most proximal of the secondary measurement electrodes (4) are mounted on the catheter element (2) 140–220 mm away from the distal end (3) of the catheter element(2).

6. Catheter according to claim 3, characterized in that five primary measurement electrodes (4) are mounted on the catheter element (2) with a mutual spacing of 4–8 mm, one of said first measurement electrodes (4) being positioned 4–8 mm away from the end (3) of the catheter element (2).

7. Catheter according to claim 3, characterized in that six secondary measurement electrodes (4) are mounted to the catheter element (2) with a mutual spacing of 20–30 mm, the distance between the primary measurement electrode (4) positioned furthest away from the distal end (3) and the secondary measurement electrodes (4) positioned closest to the distal end (3) being 20–30 mm.

8. Catheter according to claim 3, characterized in that the outflow opening (6) is made further away from the distal end (3) of the catheter element (2) than at least two of the measurement electrodes (4) fixed to the catheter element (2).

9. Catheter according to claim 3, characterized in that calibration electrodes (5) are mounted on the catheter element (2), the calibration electrodes (5) being mounted further away from the end (3) of the catheter element (2) than the outflow opening (6) and the mutual spacing between said calibration electrodes (5) being 0.1–0.5 mm.

10. Catheter according to claim 3, characterized in that the measurement electrodes (4) are annular electrodes.

11. Catheter according to claim 3 wherein, the most proximal of the secondary measurement electrodes (4) are mounted on the catheter element (2) 175 mm away from the distal end (3) of the catheter element(2).

12. Catheter according to claim 3, characterized in that five primary measurement electrodes (4) are mounted on the catheter element (2) with a mutual spacing of 5 mm, one of said first measurement electrodes (4) being positioned 5 mm away from the end (3) of the catheter element (2).

13. Catheter according to claim 3, characterized in that six secondary measurement electrodes (4) are mounted to the catheter element (2) with a mutual spacing of 25 mm, the distance between the primary measurement electrode (4) positioned furthest away from the distal end (3) and the secondary measurement electrodes (4) positioned closest to the distal end (3) being 25 mm.

* * * * *